United States Patent
Berner et al.

(10) Patent No.: US 12,066,686 B2
(45) Date of Patent: Aug. 20, 2024

(54) APPARATUS FOR VARYING A FOCAL POINT OF AN OPTICAL SYSTEM IN A DENTAL 3D-SCANNER AND DENTAL 3D-SCANNER

(71) Applicant: DENTSPLY SIRONA inc., York, PA (US)

(72) Inventors: Markus Berner, Bülach (CH); Martin Seib, Heppenheim (DE); Fabrizio Confalonieri, Heppenheim (DE)

(73) Assignee: DENTSPLY SIRONA INC., York, PA (US)

( * ) Notice: Subject to any disclaimer, the term of this patent is extended or adjusted under 35 U.S.C. 154(b) by 680 days.

(21) Appl. No.: 17/279,148
(22) PCT Filed: Sep. 27, 2019
(86) PCT No.: PCT/EP2019/076151
§ 371 (c)(1),
(2) Date: Mar. 24, 2021
(87) PCT Pub. No.: WO2020/064992
PCT Pub. Date: Apr. 2, 2020

(65) Prior Publication Data
US 2021/0389549 A1    Dec. 16, 2021

(30) Foreign Application Priority Data
Sep. 27, 2018   (EP) ..................................... 18197051

(51) Int. Cl.
*G02B 26/08*   (2006.01)
*A61B 5/00*   (2006.01)
(Continued)

(52) U.S. Cl.
CPC .............. *G02B 7/04* (2013.01); *A61B 5/0062* (2013.01); *A61B 5/0088* (2013.01); *G02B 27/646* (2013.01)

(58) Field of Classification Search
CPC .......... G02B 7/04; G02B 27/646; G02B 7/08; A61B 5/0062; A61B 5/0088; A61B 2018/20353; A61C 9/0066; A61C 9/0053
See application file for complete search history.

(56) References Cited

U.S. PATENT DOCUMENTS

2008/0090199 A1*   4/2008   Noguchi .............. A61B 5/0066
                                                    433/29
2009/0080048 A1   3/2009   Tsao
(Continued)

FOREIGN PATENT DOCUMENTS

DE           10356412 A1    6/2005
DE        102007005625 A1    8/2008
(Continued)

OTHER PUBLICATIONS

International Search Report; PCT/EP2019/076151; Nov. 21, 2019 (completed); Dec. 2, 2019 (mailed).
(Continued)

*Primary Examiner* — Euncha P Cherry
(74) *Attorney, Agent, or Firm* — DENTSPLY SIRONA INC.

(57) ABSTRACT

The present invention relates to an apparatus for varying a focal point of an optical system in a dental 3D-scanner, comprising: a lens unit with a lens being movable between a front reversal position and a rear reversal position to vary a position of a focal point with respect to a scan object; a guide unit for guiding a movement of the lens unit between the front reversal position and the rear reversal position along a guide axis being parallel to an optical axis of the lens; and a drive unit for driving the movement of the lens unit, said drive unit including a linear motor with an anchor and a stator, said anchor being movable along a drive axis of the drive unit that is parallel to the guide axis, said stator being affixed to the guide unit. The present invention further relates to a dental 3D-scanner for scanning a three-dimensional scan object.

18 Claims, 4 Drawing Sheets

(51) Int. Cl.
    *G02B 7/04*         (2021.01)
    *G02B 27/64*      (2006.01)

(56) References Cited

U.S. PATENT DOCUMENTS

| | | |
|---|---|---|
| 2009/0279103 A1 | 11/2009 | Thiel |
| 2018/0192877 A1 | 7/2018 | Atiya |
| 2019/0319529 A1* | 10/2019 | Yamano .................. H02M 1/10 |

FOREIGN PATENT DOCUMENTS

| | | |
|---|---|---|
| EP | 2051042 B1 | 11/2010 |
| EP | 2377464 A1 | 10/2011 |
| JP | 2013118779 A | 6/2013 |
| JP | 2015083978 A | 4/2015 |

OTHER PUBLICATIONS

International Preliminary Report on Patentability; PCT/EP2019/076151; Nov. 21, 2019 (completed); Dec. 2, 2019 (mailed).
Written Opinion of the International Searching Authority; PCT/EP2019/076151; Nov. 21, 2019 (completed); Dec. 2, 2019 (mailed).

* cited by examiner

APPARATUS FOR VARYING A FOCAL POINT OF AN OPTICAL SYSTEM IN A DENTAL 3D-SCANNER AND DENTAL 3D-SCANNER

CROSS-REFERENCE TO RELATED APPLICATIONS

This is a National Phase application of International Application No. PCT/EP2019/076151, filed Sep. 27, 2019, which claims the benefit of and priority to EP Application Ser. No. 18197051.8, filed on Sep. 27, 2018, which are herein incorporated by reference for all purposes.

TECHNICAL FIELD OF THE INVENTION

The present invention relates to an apparatus for varying a focal point of an optical system in a dental 3D-scanner. The present invention further relates to a dental 3D-scanner.

BACKGROUND ART OF THE INVENTION

In view of the increasing average life expectancy of the population and the technological progress, the reconstruction of teeth and the use of dentures and dental prostheses have become more and more important in recent years. For these purposes and also for other applications in the field of odontology, it is required to accurately assess the situation in a patient's mouth. Traditional approaches in this respect include making use of a soft material, in particular wax, to create an impression of the patient's jaw and remaining teeth. This impression then forms the basis for constructing a model to customize artificial dentition to the specific needs of the respective patient.

Recently, dentists and technicians in dental laboratories have more and more been relying on 3D-scanners (can sometimes also be referred to as tomography scanners) for generating a three-dimensional representation of the situation in a patient's mouth based on scan data acquired in the mouth of the patient. Such a model can. e.g., form the basis for a computer-aided prosthesis design. There exist various handheld devices to be inserted into a patient's mouth as an intraoral 3D-scanner for obtaining in-situ scan data. For instance, a camera sensor can be used to gather the respective data. Usually, the camera is manually moved around the upper or lower jaw or a section of interest of the jaws that is subject to reconstruction.

The scanning and reconstruction can. e.g., be based on fringe projection methods. Objects are illuminated with structured patterns of light. These patterns are modulated by the scan object and then recorded as an image with a camera at a known angle with respect to the projections. Techniques such as a Fourier transformation can be used to calculate the surface modulations by analyzing the recorded images. Based on these data, it is possible to obtain 3D coordinates of the scan object.

Different 3D-measurement principles require that a lens of an optical system of the image sensor is moved in order to vary a focal point (or focal plane). By moving a lens back and forth with respect to the detector (image sensor) and/or projector, it becomes possible to obtain information on the spatial dimensions of a scan object. This measurement principle corresponds to the function of a confocal microscope. If the camera is a handheld device, it is important that the lens is moved at sufficient speed so that a relative movement of the camera with respect to the scan object does not affect the measurement accuracy. Usually, oscillation frequencies of a movable lens in a dental 3D-scanner are on the order of 2-20 Hz.

In this respect, EP 2 051 042 B1 relates to a device for tomographically recording objects. The device comprises a first grid arranged in an optical axis of a light beam downstream of a source of light which the light beam may be guided through before irradiating an object so that a pattern of the first grid may be projected on the object. The device further comprises an optical imaging assembly for imaging the object on a sensor. Still further, the device comprises a second grid provided in the optical axis of the reflected light beam, the second grid having a pattern matching the first grid, the reflected light beam having the pattern of the first grid being guided through said second grid so that the sensor senses the light beam reflected by the object with a Moiré pattern resulting from overlying the pattern of the first grid and the pattern of the second grid.

One challenge with current approaches to three-dimensional scanning by means of a movable lens are vibrations. In particular for higher frequencies, the movement of the lens in a handheld scanning device can result in vibrations of the scanning devices. These vibrations can cause a blurring of the gathered data and the reconstructed 3D-scan. One approach to compensate such vibrations is to make use of a counterweight. Such a counterweight can be moved at the same speed as the lens but in the opposite direction. This, however, has the drawback that the total mass is increased so that it becomes more difficult to move the lens at an adequate oscillation frequency.

SUMMARY OF THE INVENTION

In view of the above, the present invention faces the problem of improving the image quality of a dental 3D-scanner with a movable lens. In particular, the present invention aims at reducing vibrations of a handheld scanning device for intraoral application albeit allowing a lightweight construction of the device. A high oscillation frequency and a quick reaction of the movable lens is desired to allow for a compensation of manual movements of the handheld device with respect to the scan object.

To solve this problem, a first aspect of the present invention relates to an apparatus for varying a focal point of an optical system in a dental 3D-scanner, comprising: a lens unit with a lens being movable between a front reversal position and a rear reversal position to vary a position of a focal point with respect to a scan object; a guide unit for guiding a movement of the lens unit between the front reversal position and the rear reversal position along a guide axis being parallel to an optical axis of the lens: and a drive unit for driving the movement of the lens unit, said drive unit including a linear motor with an anchor and a stator, said anchor being movable along a drive axis of the drive unit that is parallel to the guide axis, said stator being affixed to the guide unit.

In another aspect, the invention relates to a dental 3D-scanner for scanning a three-dimensional scan object, comprising: an apparatus as defined above: a detector for detecting a light signal from the scan object passing through the lens; and a handheld housing for manually guiding the 3D-scanner around the scan object.

Preferred embodiments of the invention are defined in the dependent claims. It shall be understood that the claimed dental 3D-scanner has similar and/or identical preferred embodiments as the claimed apparatus, in particular as defined in the dependent claims and as disclosed herein.

The apparatus of the present invention has a lens unit including the lens and the respective fixation that is movable between a front reversal position and a rear reversal position. This movement is guided by means of a guide unit in a direction parallel to an optical axis of the lens (guide axis). By this movement of the lens a distance between the lens and a photodetector of the dental 3D-scanner as well as a projector is varied. The distance is increased in the front reversal position. Thereby, a position of a focal point with respect to a scan object is modified. In other words, the scan object is scanned at different depths or in different planes. The movement is driven by a drive unit having a linear motor. The stator of the linear motor is affixed to the guide unit and the anchor movement is transferred to the lens unit. Usually, the lens is oscillated at an oscillation frequency while scanning the scan object. The movement of the lens is thereby limited by the distance between the front reversal position and the rear reversal position. It is, however, also possible that the lens is moved by a smaller amplitude.

The present invention is based on the idea of making use of a linear motor for moving a lens in a dental 3D-scanner. In comparison to previous approaches with piezoelectric actuators (piezo acoustic drives), approaches that are based on a link motion to transform a rotational movement into a linear movement or align actuators that are comparable to voice coil actuators, the linear motor of the present invention has the advantage that the control of the movement of the lens can be very precise and accurate. It becomes possible to freely choose a reversal point to adapt the movement of the lens to the size and position of a scan object. The position of the lens can be assessed very accurately by means of corresponding sensors. Further, high accelerations of the lens unit are possible so that high oscillation frequencies can be realized. As a result, high quality scans can be generated.

In a preferred embodiment, the drive unit includes a coupling arrangement for coupling a movement of the anchor and the lens unit so that a movement of the anchor in a fast direction is transferred to a movement of the lens in a second direction opposite to the first direction. Thus, the anchor of the linear motor is used as a counterweight to compensate for vibrations caused by the movement of the lens unit. In comparison to previous approaches that require a separate counterweight, this has the advantage that a more lightweight construction can be obtained. Furthermore, by making use of the anchor as a counterweight, the timing of the movement of the lens unit and the counterweight is ensured. Since the lens unit is driven by the counterweight, no vibrations can occur. Measurement accuracy is improved and it is ensured that a high-quality three-dimensional image of an object can be generated.

In an embodiment, the coupling arrangement includes a flexible connection element for connecting the anchor and the lens unit to transfer a force from the anchor to the lens unit. Said flexible connection element preferably includes a steel strip. A steel strip can also be referred to as a steel tape. The flexible connection element transforms or transmits the movement of the anchor to a movement of the lens unit in the opposite direction. For this, the connection element is preferably flexible in a single direction so that it can be guided around a respective deflection and is rigid with respect to its length axis so that both a compressive force and a tractive force can be forwarded from the anchor to the lens unit. A steel strip or steel band has such properties and can thus be used advantageously.

In another preferred embodiment, the coupling arrangement includes a tension element for tensioning the connection element. Said tension element preferably includes a spring. By making use of a tension element, it becomes possible to ensure that the movement of the anchor is smoothly transferred to the movement of the lens unit. No vibrations occur if the connection element is constantly held under force. In particular, when the linear movement is reversed in the opposite direction, it is important that overshooting is impeded. Preferably, a spring is used to provide this functionality. It is ensured that vibrations are minimized so that the quality of the three-dimensional scan is improved.

In an embodiment, the coupling arrangement includes an inverting element for inverting the movement of the anchor. This inverting element preferably includes a ball bearing. In order to transfer the movement from the anchor to the lens unit, it is advantageous to make use of a deflection corresponding to a change in direction. To provide this functionality, it is possible to make use of a ball bearing that minimizes fiction so that high oscillation frequencies can be obtained at low vibrations. This has the effect that a precise movement of the lens unit at high speed is assured to improve the quality of a generated 3D scan.

In yet another embodiment, the guide unit includes a position sensor for determining a position of the lens unit between the front reversal position and the rear reversal position. The position sensor preferably includes an optical distance measurement sensor. It is possible to include a position sensor to determine the position of the lens and thereby determine the position of the focal point within the guide unit. An optical distance measurement sensor may particularly correspond to a laser sensor or the like that allows for a precise determination of a distance. For instance, the position sensor can be attached to a stationary part and a light beam can be directed to a moving part of the guide unit. By making use of a position sensor, it becomes possible to control the movement of the lens unit and to adapt the movement of the lens unit to a position and shape of a current scan object. A precise measurement results in a high-quality 3D scan of the scan object.

In a preferred embodiment, the drive unit is configured to control the movement of the lens unit based on a sensor signal of the position sensor. In particular, it is advantageous if the sensor signal of the position sensor is exploited to control the movement of the lens unit. Thereby, the measured variable is directly indicative of the variable intended to be controlled, i.e. the position of the focal point or focal plane. The alternative of measuring the anchor position and exercising control based on the anchor position would, in contrast, not correspond to a direct control since the anchor movement needs to be transferred to the lens movement. The lens unit is rigidly connected to the lens so that a direct measurement of the focal point or focal plane position is obtained by making use of the sensor signal of the position sensor. A precise control is assured so that the scan quality can be further improved.

In yet another preferred embodiment, the guide unit includes a linear recirculating ball bearing guide. The lens unit includes an engaging element for engaging into said linear recirculating ball bearing guide. The linear recirculating ball bearing guide corresponds to a railing in which a respective part of the lens unit is guided along the guide axis. Friction is minimized or reduced so that a precise and fast movement of the lens unit is possible. This again has the effect that the scanning quality is improved.

In yet another preferred embodiment, a mass of the lens unit is equal to a mass of the anchor to compensate for reaction forces resulting from acceleration of the lens and the anchor. Preferably, the mass of the lens unit is chosen to be equal to the mass of the anchor. If both masses are the same, the movement in the opposite direction is entirely compensated for so that the resulting vibrations are minimized or completely prevented. Thereby, it is optionally possible to make use of additional masses (balancing masses) on either the lens unit or the anchor to ensure that the total masses of the two parts moving in opposite directions are equal. Minimized vibrations of the handheld scanner result in high-quality 3D scans.

In another preferred embodiment, a centerline of mass of the lens unit parallel to the guide axis corresponds to a centerline of mass of the anchor parallel to the guide axis. By ensuring that the centerlines of mass of the moving parts are aligned with one another, it becomes possible to compensate for hinge or torque moments. It is ensured that no torque moments are produced when the anchor and the lens unit are moved or accelerated against one another in opposite directions. The scan quality is further improved.

In another preferred embodiment, the linear motor is a brushless 3-phase linear servomotor. The linear motor preferably includes a hall sensor for measuring a position of the anchor with respect to the stator. As an additional sensor, it is possible to make use of a hall sensor in a 3-phase linear servomotor. This hall sensor can particularly be used to control the power input to the servomotor to allow for precise controllability.

In another embodiment, a maximum displacement of the anchor is equal to a distance between the font reversal position and the rear reversal position. The required construction or space is minimized if the maximum displacement of the anchor corresponds to the distance between the front reversal position and the rear reversal position. Since the movements of the two moving parts are linked, it is not required that one movement has a higher displacement than the other. The required constructional space and the total weight are minimized and manufacturing costs are reduced.

In another preferred embodiment, the drive unit is configured to drive the movement of the lens unit to oscillate between a selectable front oscillation position and a selectable rear oscillation position at an oscillation frequency of 2 to 20 Hz, preferably 5 to 10 Hz, in particular 7.5 Hz. It is not required that the oscillation is carried out at a maximum displacement. For smaller scan objects, it is sufficient if the focal point is varied so that the dimensions of the scan objects are fully covered. The advantage of making use of a smaller amplitude is that a higher frequency can be obtained. A higher frequency results in that a movement of the 3D-scanner with respect to the scan object can be compensated for. The linear motor allows for a precise selection of a front oscillation position and a rear oscillation position between which the lens unit oscillates.

In a preferred embodiment of the dental 3D-scanner, it comprises a control unit for controlling the drive unit. The control unit makes use of the different sensor signals and of a user input (optional) to control the parameters of the movement of the lens unit. In particular, it becomes possible to adjust an oscillation frequency and an amplitude of the movement of the lens unit.

Herein, a focal point of an optical system corresponds to a focal plane position. The focal point of focal plane represents the distance at which an image or an object is focused. A scan object can particularly be a single tooth, a plurality of teeth or a human jaw. It is possible to apply the principles of the present invention to other areas in which a movable lens of a dental 3D-scanner is integrated in a handheld housing so that higher oscillation frequencies of the lens are required to compensate for movements of the housing caused by the operator of the 3D-scanner. For instance, the principles of the present invention can also be used in an industrial 3D-scanner.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
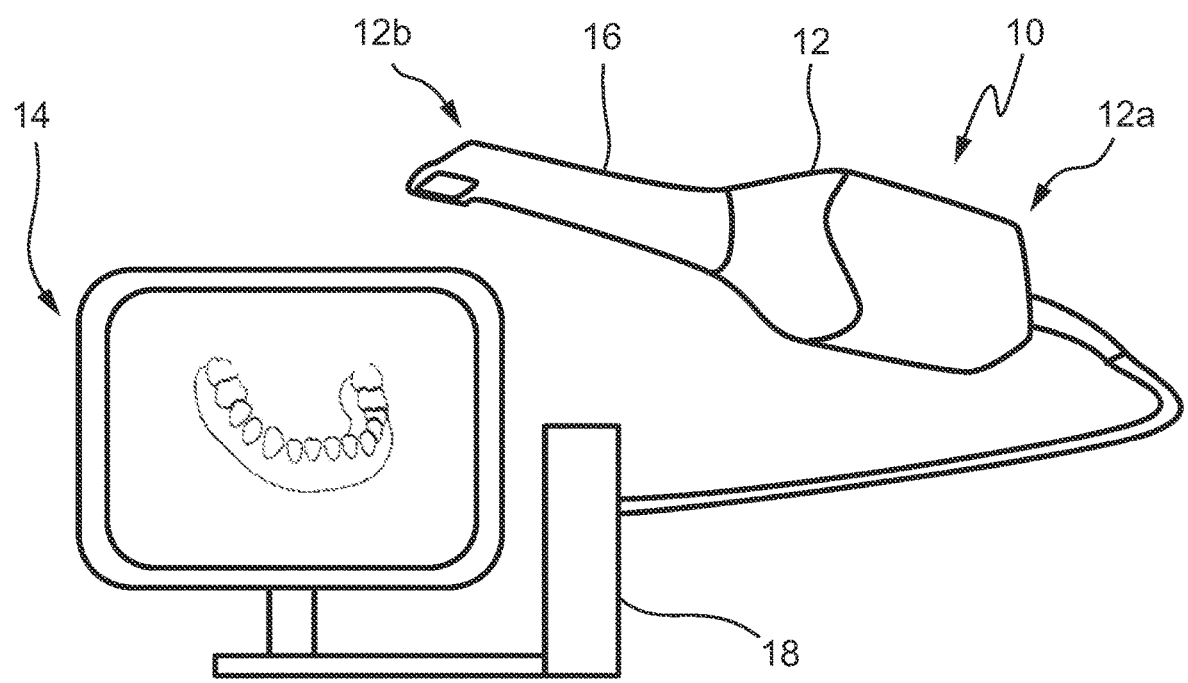
FIG. 1 shows a schematic illustration of a dental 3D-scanner according to an aspect of the present invention.

In FIG. 1, a dental 3D-scanner 10 for scanning a 3-dimensional scan object according to the present invention is schematically illustrated. The dental 3D-scanner 10 includes a handheld housing 12. In the illustrated example, the handheld housing 12 has a widening rear section 12*a* to be held in the hand of an operator and a tapered front section 12*b* to be inserted into the mouth of a patient. Attached to the rear section 12*a* is a cable via which the handheld housing 12 is connected to a control device 14 that can, e.g., correspond to a personal computer. The dental 3D-scanner 10 has a window in its tapered front section 12*b* through which a light signal can pass and can reach a detector 16 inside the handheld housing 12. The dental 3D-scanner 10 is controlled by a control unit 18 that, in the illustrated example, is included in the control device 14.

The dental 3D-scanner 10 of the present invention can particularly be put to use in a dentist's surgery or also in a dental laboratory to obtain an in-situ scan of a situation in the mouth of a patient. Usually, the situation in the mouth of a patient is scanned intraorally. It is, however, also possible that a scan object outside the mouth of a patient is scanned. The handheld housing 12 is hand-guided by a dentist or dental technician that moves the 3D-scanner around the scan object. This allows to obtain an in-situ scan to obtain a 3D representation. It is advantageous if a live visualization of the scan object, in particular the teeth or the jaw of the patient, is displayed on a screen during the data collection as schematically illustrated.

It is to be understood that the illustrated embodiment is an example and that it is also possible that the different components are arranged in a different way. For instance, it is possible that the handheld housing 12 includes the control unit 18 and/or that the handheld housing 12 is connected via a wireless connection with the control device 14. Also, it is possible that the handheld housing 12 includes all components of the dental 3D-scanner and that only an image of the scan object is transferred to a separate external screen.

Figure 2:
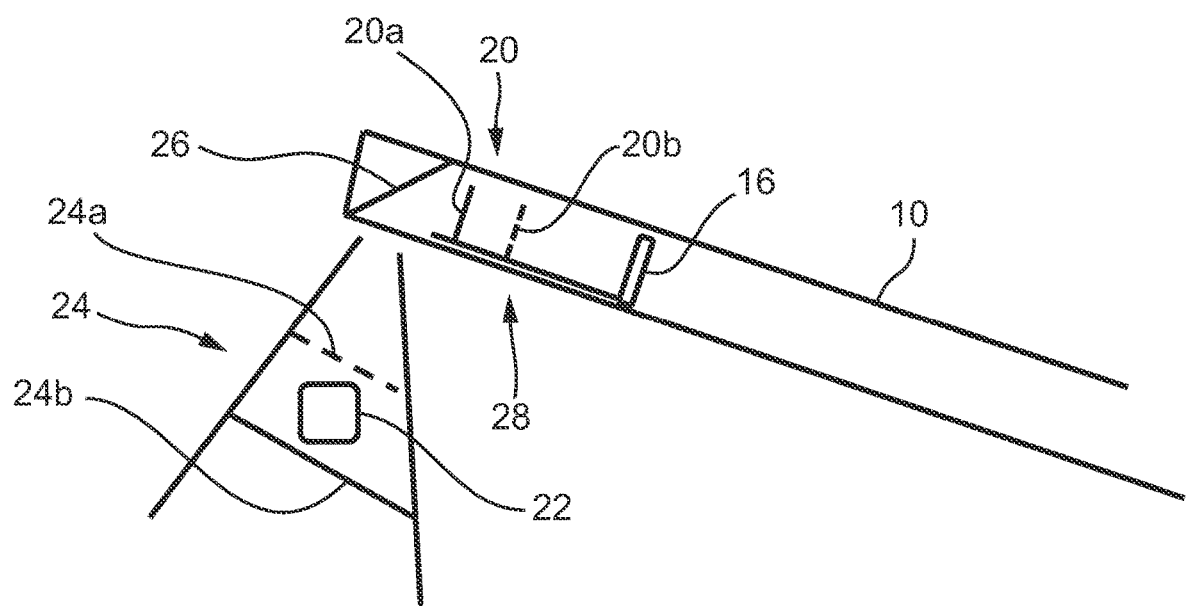
FIG. 2 shows a schematic illustration of a measurement principle based on a moving lens in a 3D-scanner.

In FIG. 2, the measurement principle of the dental 3D-scanner 10 is schematically illustrated. The dental 3D-scanner 10 has a lens 20 through which a light signal from a scan object 22 passes prior to reaching the detector 16. The scan process thereby is based on a variable focal point 24. The focal point 24 corresponds to a focal plane. The focal point 24 is varied so that the entire spatial dimension of the scan object 22 is sampled. In other words, the image obtained by means of the detector 16 is focused at variable distances from the 3D-scanner 10 or its detector 16, respectively. The measurement principle thereby corresponds to a confocal microscope. Usually, the lens oscillates to periodically vary the focal point.

In the illustrated embodiment, the lens 20 is moved between a front oscillation position 20a and a rear oscillation position 20b. By moving the lens 20, the focal point 24 is moved from a first position 24a above the scan object 22 to a second position 24b below the scan object 22 or the area of interest of the scan object 22. Usually, the lens 20 oscillates between the two positions at a constant oscillation frequency so that a constant sampling of the scan object 22 is obtained. Since the dental 3D-scanner 10 is not fixed in its position versus the scan object 22 but manually moved around the scan object 22 to allow for manual intraoral application, the oscillation frequency is thereby in the order of 10 Hz. By making use of such a comparatively high oscillation frequency, a blurring of the obtained scan due to movements of the scanner versus the scan object 22 is avoided. In the illustrated embodiment, a mirror 26 is arranged between the lens 20 and the scan object 22. The movement of the lens 20 is thereby obtained by means of an apparatus 28 for varying a focal point of an optical system according to the present invention.

Figure 3:
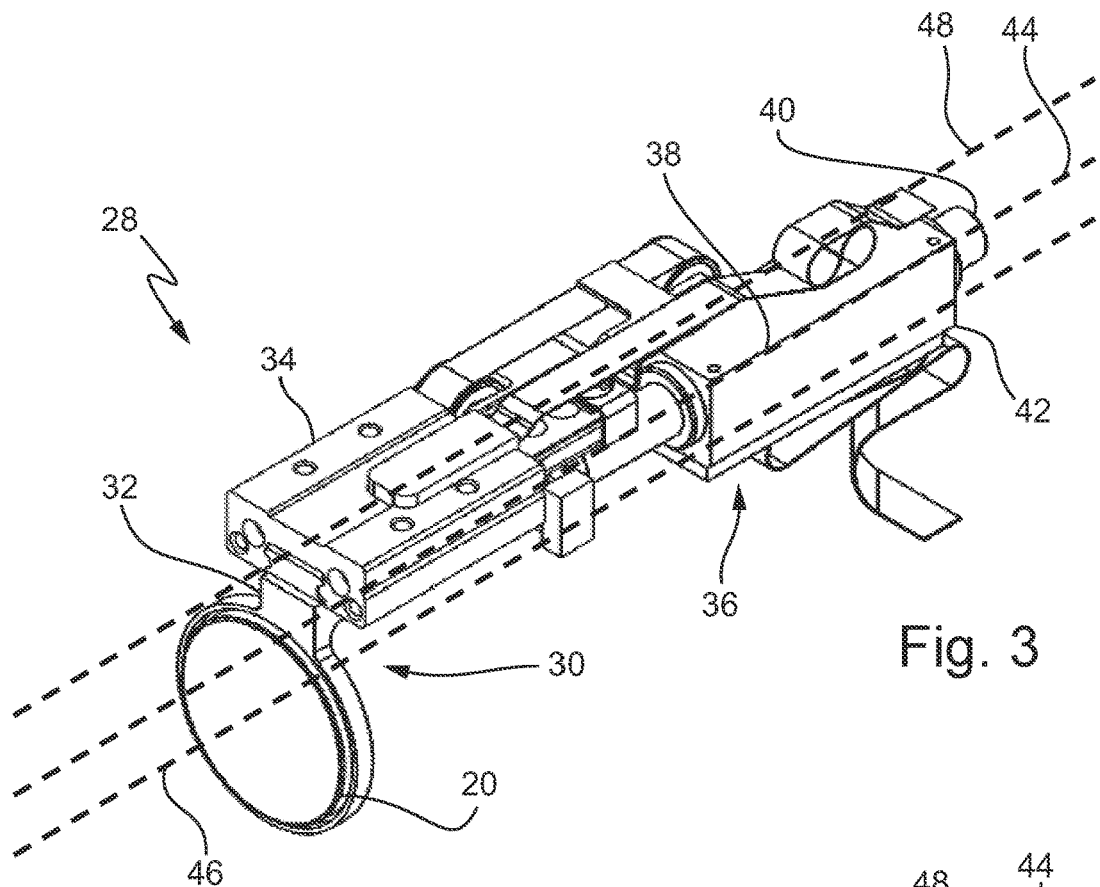
FIG. 3 shows a schematic perspective illustration of an apparatus according to the present invention with a lens unit in the rear reversal position.
Figure 4:
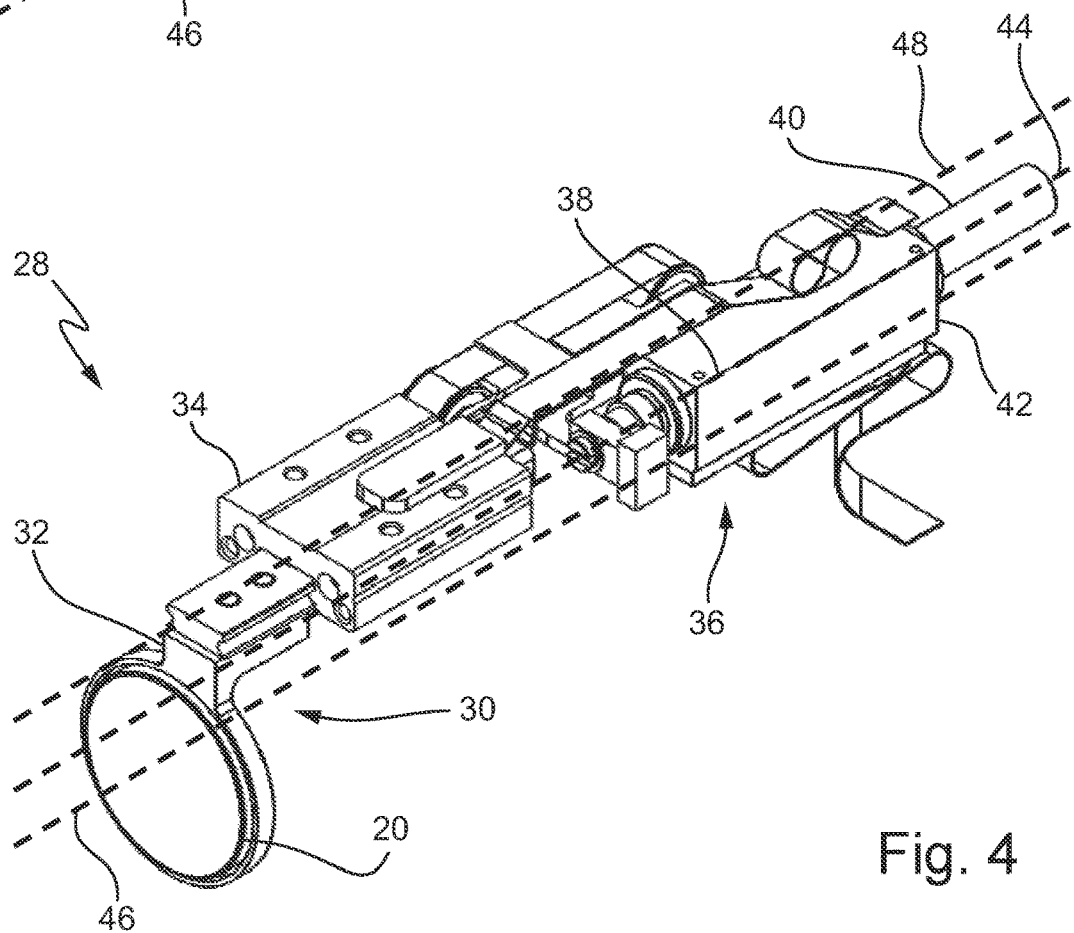
FIG. 4 shows a schematic perspective illustration of the apparatus with a lens unit in the front reversal position.

In FIGS. 3 and 4, the apparatus 28 for varying a focal point of an optical system in the dental 3D-scanner of the present invention is schematically illustrated in a perspective view. The apparatus 28 includes a lens unit 30 with a lens 20 and a corresponding holding arrangement 32 for holding the lens 20, a guide unit 34 for guiding the movement of the lens unit 30 and a drive unit 36 for driving the movement.

The lens unit 30 thereby includes all movable parts. The lens unit 30 is movable between a front reversal position as illustrated in FIG. 4 and a rear reversal position as illustrated in FIG. 3. In the front reversal position, the distance to a detector (not illustrated in the FIGS.) is increased so that the focal point of the optical system formed by the lens 20 and the detector is moved further away from the lens.

The drive unit 36 includes a linear motor 38 with an anchor 40 and a stator 42. The anchor 40 is moved versus the stator 42 along a drive axis 44. Usually a 3-phase linear servomotor is used as the linear motor 38. The linear motor 38 may include a hall sensor 39 (not illustrated) that is integrated with the linear motor housing and that provides a sensor signal to be used for controlling the power supply of the linear motor 38. The movement induced by the drive unit 36 is parallel to the drive axis 44. Thereby, the drive axis 44 is parallel to an optical axis 46 of the lens 20 and a guide axis 48 along which the movement of the lens unit 30 is guided by the guide unit 34. The optical axis 46 of the lens 20 runs through the center of the lens 20.

As illustrated in FIGS. 3 and 4, the linear movement of the lens unit 30 between the front reversal position and the rear reversal position is in the opposite direction of the movement of the anchor 40. When the lens unit 30 is moved forward, the anchor 40 is moved backward as illustrated in FIG. 4. By making use of this counter movement, it becomes possible to compensate for vibrations caused by the mass of the lens unit 30 when it oscillates. Preferably, a mass of the lens unit 30 is thereby equivalent to a mass of the anchor 40 so that optimal vibration cancellation is obtained. It is possible to add weight to one of the anchor 40 and the lens unit 30.

On the one hand, it is possible that the lens unit 30 is moved between the front reversal position and the rear reversal position. Thereby, the distance between the front and rear reversal positions represents a maximum displacement. It is, however, also possible that the linear motor 38 is controlled so that the movement of the lens unit 30 is subject to a smaller displacement. The use of a linear motor 38 has the advantage that the movement of the lens unit 30 can be inverted at any desired position between the front and rear reversal positions. In this respect, a front and rear oscillation position correspond to positions in which the movement of the lens unit 30 is inverted. The distance between the front and rear oscillation positions is smaller than the distance between the front and rear reversal positions.

Figure 5:
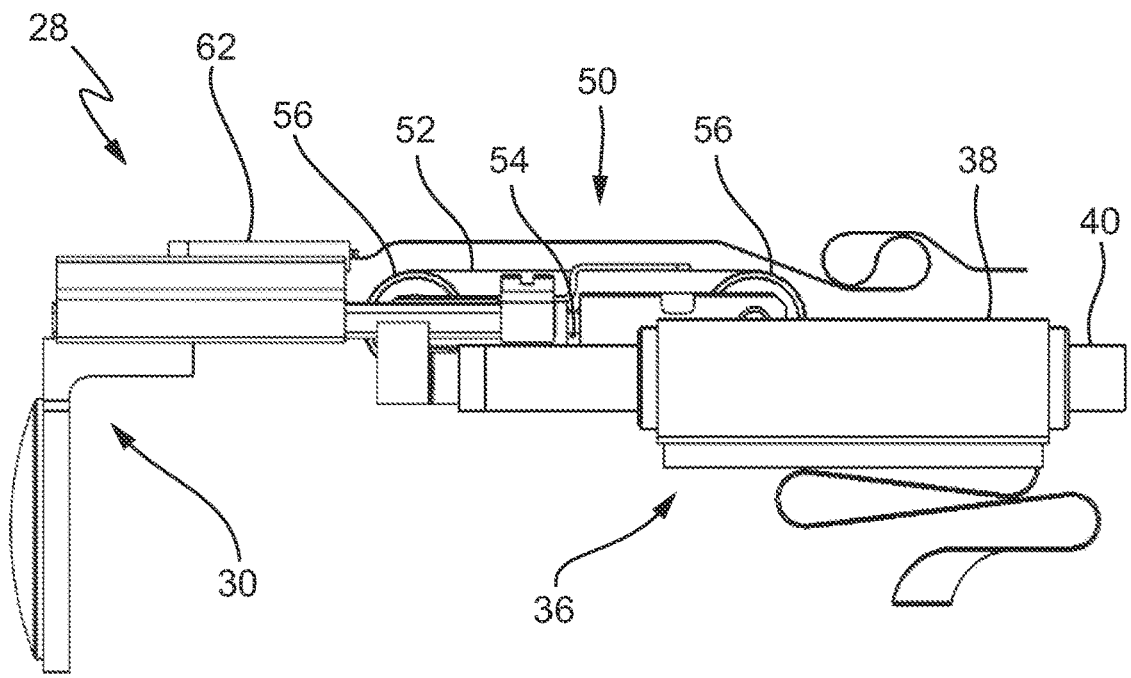
FIG. 5 shows a schematic side view of the apparatus.

In FIG. 5, the apparatus 28 is illustrated in a schematic side view to further describe the motion of the lens unit 30 and drive unit 36. In order to transform the movement of the anchor 40 in a rear direction (right in the illustration in FIG. 5) into a movement of the lens unit 30 in a front direction (left), it is required to invert the movement. For this, a coupling arrangement 50 of the drive unit 36 is arranged between the linear motor 38 and the lens unit 30.

The coupling arrangement 50 may particularly include a flexible connection element 52 which transfers the force from the anchor 40 to the lens unit 30. In the illustrated embodiment, the flexible connection element 52 is a steel strip which is sufficiently strong to transport the recurrent forces at higher oscillation frequencies and which allows transferring both tractive and compressive forces. The coupling arrangement 50 preferably includes a tension element 54 which comprises a spring in the illustrated embodiment. The tension element 54 is used to exert a force on the flexible connection element 52 so that this flexible connection element 52 is under tension and can transfer forces without shaking. This is particularly important when the movement of the lens unit 30 is inverted in the front or rear reversal positions or in the front or rear oscillation positions.

The coupling arrangement 50 further includes an inverting element 56 which comprises a ball bearing in the illustrated embodiment. This inverting element 56 inverts the movement of the anchor 40 by guiding the flexible connection element 52 through a 180° direction change. In the illustrated embodiment, two ball bearings are used.

Figure 6:
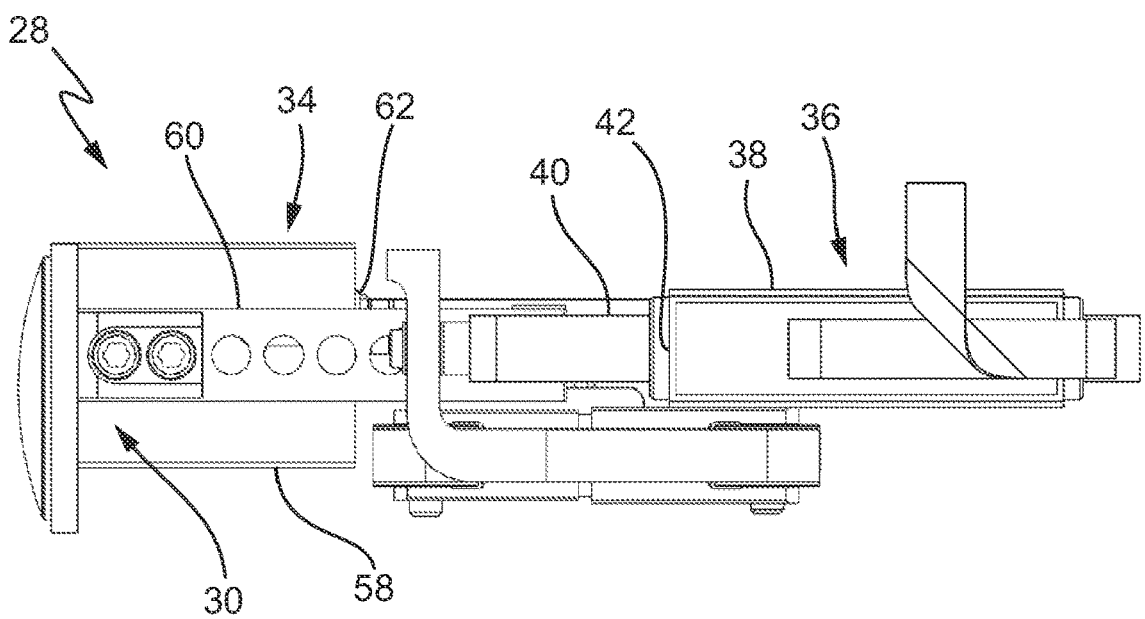
FIG. 6 shows a schematic top view of the apparatus.

In FIG. 6, the functionality of the guide unit 34 is illustrated based on a top view of the apparatus 28. The guide unit 34 connects the lens unit 30 and the drive unit 36. The guide unit 34 is affixed to the stator 42 of the linear motor 38. The lens unit 30 and the anchor 40 of the linear motor 38 are moved with respect to the guide unit 34 and the stator 42.

In the illustrated embodiment, the guide unit 34 includes a recirculating ball bearing guide 58 in which an engaging element 60 of the lens unit 30 is guided. The linear recirculating ball bearing guide 58 thereby functions comparable to a railing. By making use of a ball bearing, friction is minimized so that high oscillation frequencies are possible.

Furthermore, the guide unit 34 includes a position sensor 62 which allows obtaining information on a position, in particular a lateral position, of the lens unit 30 with respect to the guide unit 34. In the illustrated embodiment, the position sensor 62 is an optical sensor that measures a distance. This position of the lens unit 30 is direct measure of the current position of the lens and the focal point as well as the current position of the anchor 40 of the linear motor 38. The sensor signal of the position sensor 62 can be used to control the drive unit 36 so that a direct feedback and control loop becomes possible. In particular, it is possible to specify specific front and rear oscillation positions and control the current position to decide whether to move in the other direction based on the sensor signal of the position sensor. Thereby, the corresponding control can be exercised in a control unit that can also be included in a dental 3D-scanner or that can be externally arranged in a separate processing device.

Figure 7:
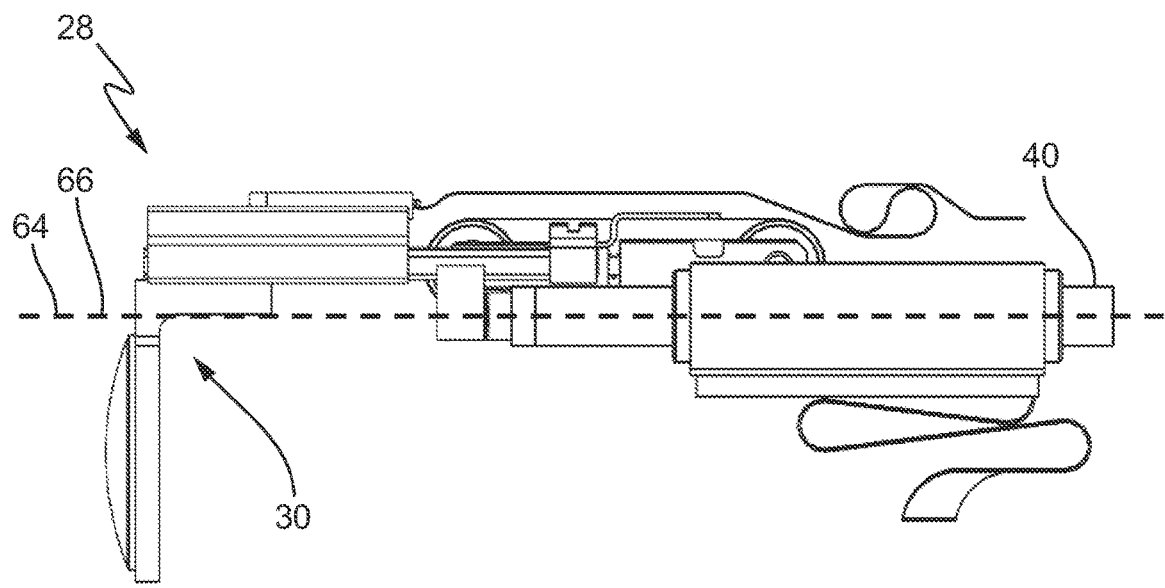
FIG. 7 shows a schematic illustration of the positions of the centerlines of mass in a side view.
Figure 8:
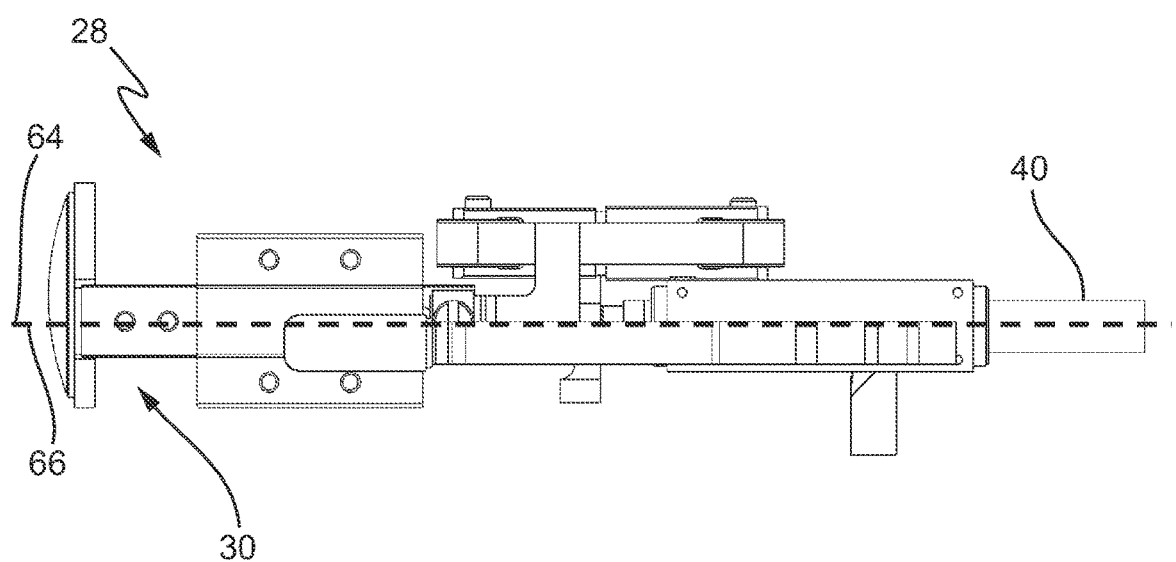
FIG. 8 shows a schematic illustration of the positions of the centerlines of mass in a bottom view.

In FIGS. 7 and 8, the apparatus 28 is schematically illustrated in a side view (FIG. 7) and in base view (FIG. 8). In order to minimize torque moments and rotational forces that could also result in vibrations of the dental 3D-scanner, it is advantageous that a centerline of mass 64 of the anchor 40 is equal to a centerline of mass 66 of the lens unit 30. The centerlines of mass 64, 66 are thereby parallel to the guide axis. As illustrated in the two different views in FIGS. 7 and 8, the centerline of mass 64 of the anchor and the centerline of mass 66 of the lens unit are equal both in the side view and in the bottom view. This construction allows preventing torque forces from occurring.

The foregoing discussion discloses and describes merely exemplary embodiments of the present disclosure. As will be understood by those skilled in the art, the present disclosure may be embodied in other specific forms without departing from the spirit or essential characteristics thereof. Accordingly, the description is intended to be illustrative, but not limiting the scope of the disclosure, as well as other claims. The disclosure, including any readily discernible variants of the teachings herein, defines, in part, the scope of the foregoing claim terminology such that no inventive subject matter is dedicated to the public.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

The invention claimed is:

1. Apparatus for varying a focal point of an optical system in a dental 3D-scanner, comprising:
    a lens unit with a lens being movable between a front reversal position and a rear reversal position to vary a position of a focal point with respect to a scan object;
    a guide unit for guiding a movement of the lens unit between the front reversal position and the rear reversal position along a guide axis being parallel to an optical axis of the lens; and
    a drive unit for driving the movement of the lens unit, said drive unit including a linear motor with an anchor and a stator, said anchor being movable along a drive axis of the drive unit that is parallel to the guide axis, said stator being affixed to the guide unit
    wherein the drive unit includes a coupling arrangement for coupling a movement of the anchor and the lens unit so that a movement of the anchor in a first direction is transferred to a movement of the lens in a second direction opposite to the first direction.

2. Apparatus as claimed in claim 1, wherein
    the coupling arrangement includes a flexible connection element for connecting the anchor and the lens unit to transfer a force from the anchor to the lens unit.

3. Apparatus as claimed in claim 2, wherein
    the coupling arrangement includes a tension element for tensioning the flexible connection element.

4. Apparatus of claim 1, wherein
    the coupling arrangement includes an inverting element for inverting the movement of the anchor.

5. Apparatus as claimed in claim 1, wherein
    the guide unit includes a position sensor for determining a position of the lens unit between the front reversal position and the rear reversal position.

6. Apparatus as claimed in claim 5, wherein the drive unit is configured to control the movement of the lens unit based on a sensor signal of the position sensor.

7. Apparatus as claimed in claim 1, wherein
    the guide unit includes a linear recirculating ball bearing guide; and
    the lens unit includes an engaging element for engaging into said linear recirculating ball bearing guide.

8. Apparatus as claimed in claim 1, wherein a mass of the lens unit is equal to a mass of the anchor to compensate reaction forces resulting from accelerations of the lens and the anchor.

9. Apparatus as claimed in claim 1, wherein a centerline of mass of the lens unit parallel to the guide axis corresponds to a centerline of mass of the anchor parallel to the guide axis.

10. Apparatus as claimed in claim 1, wherein
    the linear motor is a brushless 3-phase linear servomotor; and
    the linear motor preferably includes a hall sensor for measuring a position of the anchor with respect to the stator.

11. Apparatus as claimed in claim 1, wherein a maximum displacement of the anchor is equal to a distance between the front reversal position and the rear reversal position.

12. Apparatus as claimed in claim 1, wherein the drive unit is configured to drive the movement of the lens unit to oscillate between a selectable front oscillation position and a selectable rear oscillation position at an oscillation frequency of 2 to 20 Hz.

13. Dental 3D-scanner for scanning a three-dimensional scan object, comprising:
    an apparatus as claimed in claim 1;
    a detector for detecting a light signal from the scan object passing through the lens; and
    a handheld housing for manually guiding the 3D-scanner around the scan object.

14. Dental 3D-scanner as claimed in claim 13, comprising a control unit for controlling the drive unit.

15. Apparatus of claim 2, wherein said connection element includes a steel strip.

16. Apparatus of claim 3, wherein said tension element includes a spring.

17. Apparatus of claim 4, wherein said inverting element includes a ball bearing.

18. Apparatus of claim 5, wherein the position sensor includes an optical distance measurement sensor.

* * * * *